(12) United States Patent
Nath

(10) Patent No.: US 6,571,049 B1
(45) Date of Patent: May 27, 2003

(54) WAVEGUIDE WITH HAND SWITCH

(76) Inventor: Gunther Nath, Otto Heilmann Str. 3, Munchen (DE), 82031

(*) Notice: Subject to any disclaimer, the term of this patent is extended or adjusted under 35 U.S.C. 154(b) by 0 days.

(21) Appl. No.: 09/806,901
(22) PCT Filed: Oct. 11, 1999
(86) PCT No.: PCT/DE99/03266
§ 371 (c)(1), (2), (4) Date: Apr. 5, 2001
(87) PCT Pub. No.: WO00/22343
PCT Pub. Date: Apr. 20, 2000

(30) Foreign Application Priority Data

| Oct. 9, 1998 | (DE) | 198 46 580 |
| Oct. 27, 1998 | (DE) | 198 49 569 |
| Nov. 6, 1998 | (DE) | 198 51 365 |
| Apr. 30, 1999 | (DE) | 199 19 817 |

(51) Int. Cl.$^7$ ............ F21V 8/00; A61C 19/00; G02B 6/10
(52) U.S. Cl. ............ 385/139; 250/504 H; 250/504 R
(58) Field of Search ............ 385/139; 335/205, 335/206, 207; 250/504 H, 504 R

(56) References Cited

U.S. PATENT DOCUMENTS

| 3,681,724 A | * | 8/1972 | Shepard ............ 335/206 |
| 4,233,493 A | * | 11/1980 | Nath ............ 219/121.6 |
| 4,623,795 A | * | 11/1986 | Knopp et al. ............ 250/493.1 |
| 5,444,263 A | * | 8/1995 | Mastnak ............ 250/493.1 |
| 5,591,219 A | * | 1/1997 | Dungan ............ 250/504 H |
| 5,912,470 A | * | 6/1999 | Eibofner et al. ............ 250/492.1 |

* cited by examiner

*Primary Examiner*—Tulsidas Patel
*Assistant Examiner*—Michael C. Zarroli
(74) *Attorney, Agent, or Firm*—Galvin & Palmer

(57) ABSTRACT

Described is an optical waveguide for an optical lighting arrangement comprising a freely rotatable tube (6) arranged at the light exit end of the optical waveguide (2). The optical waveguide (2) is characterized in that the tube (6) comprises a non-magnetic material, wherein the optical waveguide (2) has a hand switch for controlling the radiation flux of the optical lighting arrangement, which is formed by a magnetically activatable switch (27) which is disposed between the optical waveguide (2) and the tube (6) and which is fixed on the outer peripheral surface of the optical waveguide (2) and spaced from the inside surface of the tube (6), and an annular magnet (26) which is disposed on the tube (6) and which bears snugly against the tube (6) and is displaceable axially thereon. Two thin wires or stranded conductors (41, 42) extend from the magnetically activatable switch (27) and extend in the interior of the optical waveguide (2) but outside the liquid thereof to the light entry end.

24 Claims, 12 Drawing Sheets

WAVEGUIDE WITH HAND SWITCH

CROSS-REFERENCE TO RELATED APPLICATIONS

None

STATEMENT REGARDING FEDERALLY SPONSORED RESEARCH OR DEVELOPMENT

Not applicable

REFERENCE TO A "SEQUENTIAL LISTING," A TABLE, OR A COMPUTER PROGRAM LISTING APPENDIX SUBMITTED ON A COMPACT DISK

None

BACKGROUND OF THE INVENTION (1) Field of the Invention

The invention concerns an optical waveguide.

(2) Description of the Related art including information discussed under 37 CFR 1.97 and 1.98

Radiation polymerization devices in the form of optical illuminating arrangements with coupled flexible optical waveguides have already been known for a relatively long time both in industry and also in dentistry; see in that respect German laid-open applications DE-A1 30 09 171.5 and DE-A1 40 14 363.5, and utility model No G 94 00 445.5.

The radiation sources used for the radiation polymerization devices are either tungsten-halogen lamps, high-pressure xenon lamps or medium-pressure or high-pressure mercury lamps. In dentistry, it is predominantly light radiation in the blue spectral range, that is to say in the range of 400 nm<$\lambda$<500 nm that is used for the polymerization of filling materials (so-called composite materials), while for hardening industrial adhesives with radiation it is mostly UV-radiation in the wavelength range of 250 nm<$\lambda$<400 nm that is used. Both conventional glass fiber bundles or bundles of plastic fibers but also the liquid optical waveguides which have now been known for about 20 years can be coupled to the radiation source, as the flexible optical waveguides. The liquid optical waveguides can transmit both blue light and also UV-radiation with a high level of efficiency, in contrast to the glass fiber bundles.

Application of the radiation to the monomer is almost always controlled in respect of time by way of an adjustable timer, in which respect either the lamp is switched on for a defined time or, in the case of a continuously operated radiation source such as for example a mercury lamp, the light flow is opened by a shutter (light barrier) for a defined time, with the shutter being controlled by the timer. Triggering of the radiation dose to be applied is almost always effected either by way of a hand switch or by way of a foot switch, that is to say a closing device which functions galvanically. In the case of fiber bundle waveguides when used in dental practice use is made of both hand switches at the light exit end of the optical waveguide, and also foot switches. When liquid optical waveguides are used in dental practice, it is exclusively foot switches that are used, because, by virtue of their lower degree of flexibility and their low level of axial twistability, liquid optical waveguides all have a handle or handpiece which in the form of a rotatable tube. Thus the use of a galvanically functioning hand switch on that rotatable tube is technically burdensome and complicated because it is to be possible to actuate the hand switch in all rotational positions of the rotary tube.

BRIEF SUMMARY OF THE INVENTION

The object of the invention is to provide an optical waveguide having a hand switch, which satisfies the specified requirements and which in particular is easy and economically advantageous to operate.

That object is attained by an optical waveguide as set forth in claim 1. Further developments of the hand switch according to the invention are described in the appendant claims.

The optical waveguide according to the invention, with hand switch, is suitable in particular for use in relation to liquid optical waveguides in dental practice for hardening fillings. However it also has advantages in terms of technical industrial uses of the liquid optical waveguide for hardening adhesives, in which the optical waveguide is guided by hand (for example when "soldering" boards with optical adhesives). The novel hand switch can be used not only for liquid optical waveguides but also waveguides made up of fiber bundles although they are particularly advantageous for liquid optical waveguides.

BRIEF DESCRIPTION OF THE SEVERAL VIEWS OF THE DRAWINGS

The invention is described in greater detail hereinafter by means of preferred embodiments illustrated in the drawings in which.

DETAILED DESCRIPTION OF THE INVENTION

Figure 1:
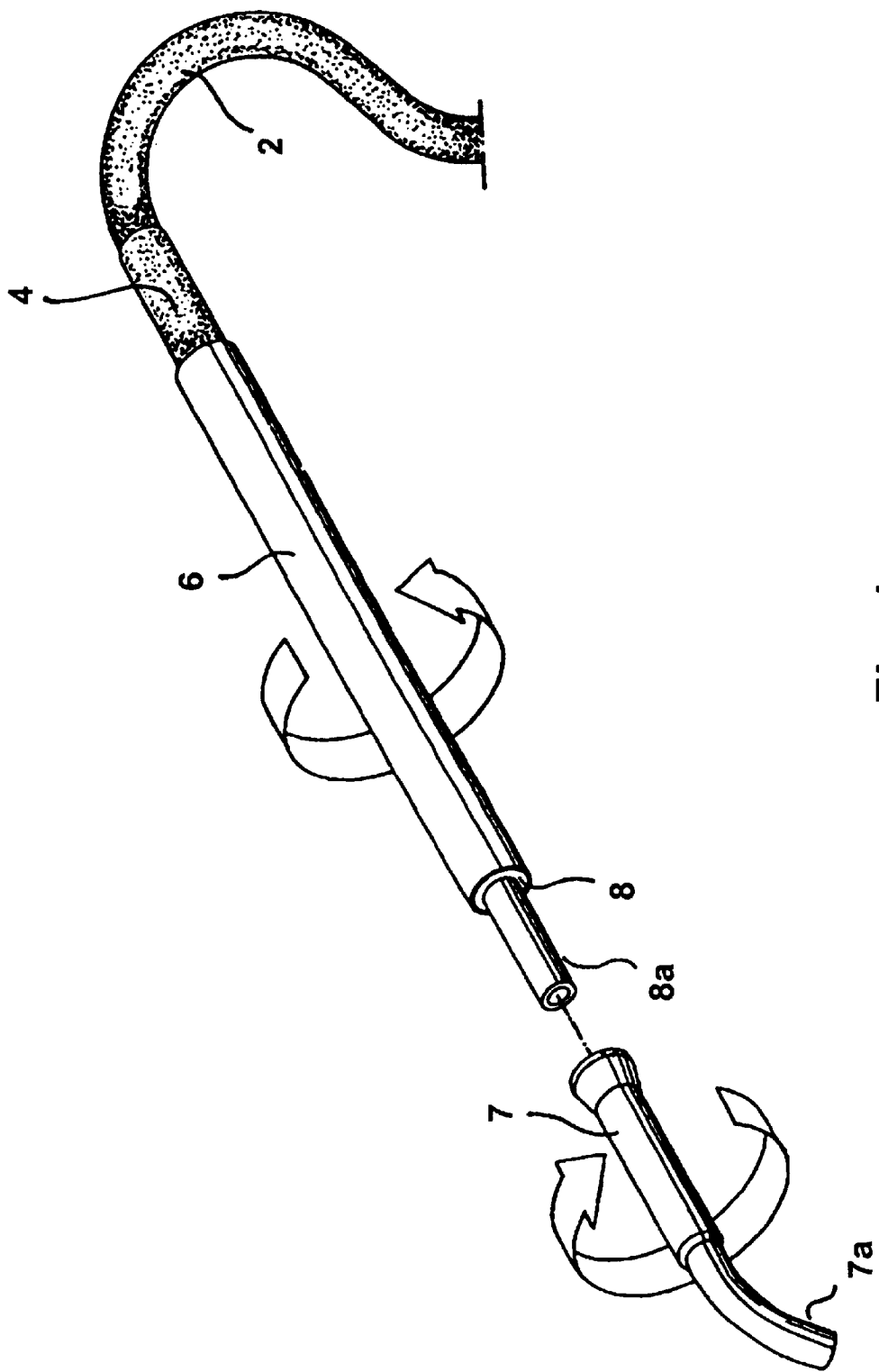
FIG. 1 shows the light exit end of a liquid optical waveguide.

Referring to FIG. 1, shown therein is the light exit end of a liquid optical waveguide of the conventional known dental design configuration. The liquid optical waveguide 2 is made up of a plastic hoze comprising a carbon/fluorine polymer filled with a liquid which has a relatively high refractive index such as for example triethyleneglycol with some water. The hoze comprising the C/F-polymer with the low refractive index is in turn disposed for reasons of mechanical reinforcement in the interior of a flexible metal wound hoze (similar to a shower pipe) which bears closely against the polymer hoze and which in turn has PVC or silicone shrunk thereover. The optical waveguide terminates at the light exit in a rigid elongate end portion 4 over which is fitted a tube 6 which is mounted freely rotatably along the axis of the optical waveguide. Disposed at the end of the tube 6 is a curved application portion 7 with an application window 7a. Curved application portion 7 is fitted over the optical waveguide end 8a, with mechanical fixing being implemented by way of a magnetic ring 8. The application portion 7 can accordingly also be rotated along the axis of the optical waveguide and relative to the tube 6, as is indicated in FIG. 1.

If the tube 6 is rotated then the curved application window 7a also rotates, which facilitates application of the radiation in situ, from the point of view of the dentist who holds the tube 6 similarly to a pencil. Rotatability of the tube 6 is so important precisely in relation to the liquid optical waveguide, because that waveguide is noticeably less flexible than for example glass fiber bundle waveguides and also in contrast thereto it can in itself be twisted only against a high level of resistance. Therefore, optical waveguides comprising glass fiber bundles always have a rigid handle or handpiece which is not rotatable relative to the axis of the optical waveguide, with a curved application window which is fixedly connected to the handpiece. In the case of glass fiber bundle optical waveguides, that facilitates mounting a hand switch which functions galvanically, in which case disposed on the handpiece of the optical waveguide is a simple electrical contact switch from which two thin wires are taken back to the lamp housing along the optical waveguide.

In general terms, in dental practice when implementing polymerization with optical waveguide devices the hand switch at the end of the optical waveguide is preferred over a foot switch because operation with the hand switch is substantially more pleasant for the dentist. In order also to make operation with the liquid optical waveguide more pleasant for the dentist, the burdensome foot switch used in relation to the polymerization device is eliminated and the structure according to the invention as set forth hereinafter of a hand switch for optical waveguides will be described, in particular for those having a rotatable tube 6.

The optical waveguide according to the invention has a hand switch for controlling the flow of radiation of an optical lighting arrangement, the switch being of the design configuration set out below.

Disposed in the interior of the rotatable tube is a magnetically activatable switch—preferably a reed switch or a Hall switch—and also at least one annular magnet which can be moved by finger pressure along the rotatable tube so that the spacing between the magnetically activatable switch and the annular magnet is reduced or increased and thus the magnetically activatable switch can be opened or closed depending on the respective strength of the magnetic field at the location of the switch.

In accordance with a first preferred embodiment the annular magnet is coupled to an elastic return force so that, after the finger pressure is removed, the annular magnet of its own accord moves back into its initial position again. The return force can be produced by a spiral spring.

Figure 2:
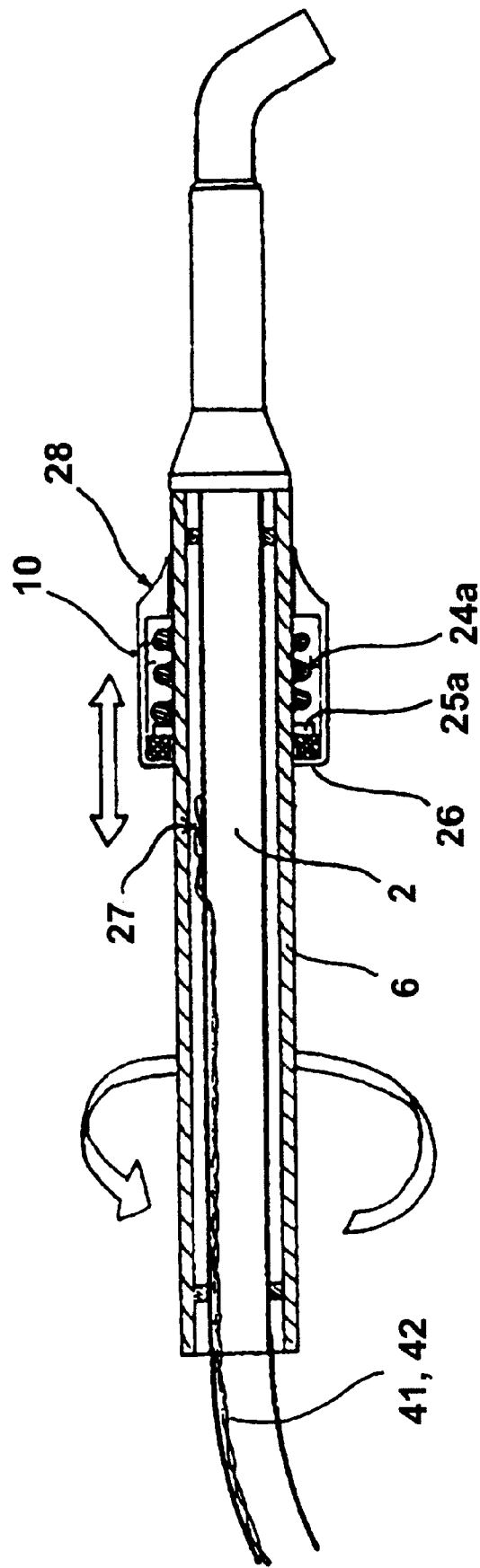
FIG. 2 shows a liquid optical waveguide according to the invention with a hand switch having a spiral spring as a return device.

Such an embodiment is shown in FIG. 2. This view clearly illustrates the arrangement of a magnetically activatable switch 27 at the light exit end of a liquid optical waveguide with a rotatable tube 6, as is used in dental practice for hardening fillings.

The liquid optical waveguide 2 opens at the light exit end into the rotatable tube 6 which comprises aluminum, plastic, high-quality steel or some other non-magnetizable material, with aluminum being preferred. Disposed between the optical waveguide 2 and the rotatable tube 6 is a magnetically activable switch 27 (sometimes also referred to as a reed switch or reed contact) which is fixedly secured on the outside peripheral surface of the optical waveguide 2 at a small spacing relative to the inside surface of the rotatable tube 6.

From the switch 27, two thin wires 41, 42 pass into the interior of the optical waveguide 2 and are there passed in the space between its liquid-filled hoze of carbon/fluorine polymer and its outer protective hoze to the light entry end of the optical waveguide where they are taken out of the optical waveguide and reinforced or sheathed with a shrink tube, a cable clamp for relieving pulling force thereon and an electrical plug, for example in the form of a jack plug. The jack plug makes it possible to make contact with the jack socket of an electrical light box which was originally provided for the foot switch.

The trigger portion of the switch is in the form of a displaceable sleeve 10 which bears snugly against the tube 6 and in the interior of which are disposed an annular permanent magnet 26 and a spiral spring 24a. The sleeve 10 also carries at the light exit end a rotationally symmetrical finger grip recess 28 and optionally knurling or ribbing 28a which extends therearound on the outer periphery (shown in FIG. 3).

The magnet ring 26 and the spiral spring 24a are separated by a stopper ring 25a which is fixedly connected to the tube 6. That gives rise to the elastic return force for the displaceable sleeve 10 if the switch 27 is to be opened again, by releasing the sleeve 10.

In the case of the hand switch shown in FIG. 2 full rotatability of the tube 6 is maintained, and it can be actuated in an ergonomically satisfactory manner with the tube 6 in any rotational position. The pencil-like handpiece which is preferred by most dentists can in that way be equipped with and offered with a hand switch. That applies in particular when using liquid optical waveguides with a rotatable tube 6.

In accordance with a second preferred embodiment of the optical waveguide according to the invention the annual movable magnet is coupled to a magnetic return force so that, when the finger pressure is removed, it of its own accord moves back again into its initial position and it thus also has a defined zero position. The magnetic return force is produced by a second annular magnet which however is fixed in position.

Figure 3:
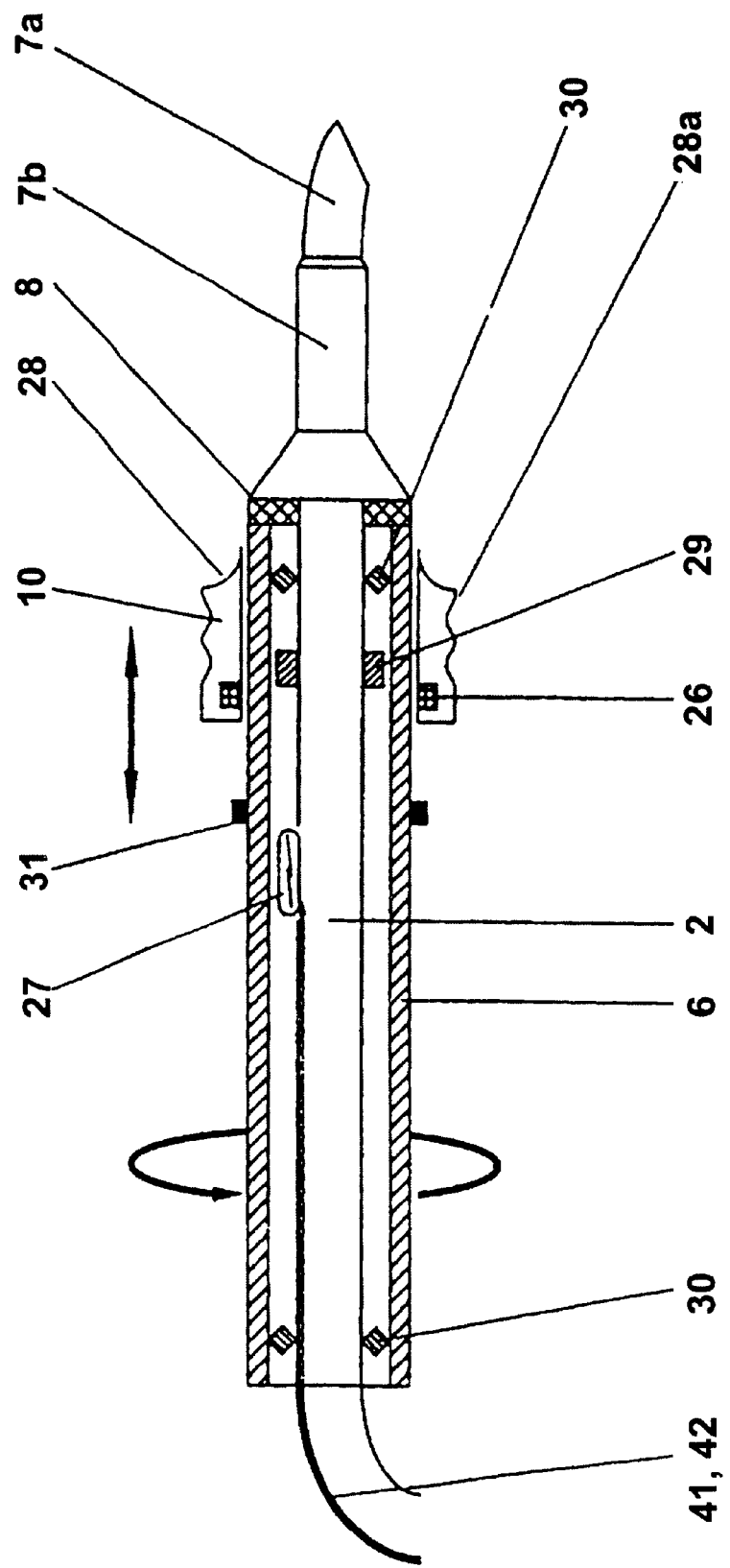
FIG. 3 shows a liquid optical waveguide according to the invention having a hand switch which has two magnets.

Such an embodiment is shown in FIG. 3. Insofar as FIG. 3 is identical to FIG. 2, the relevant structure will not be described again here and reference will be made to the description relating to FIG. 2; the same parts are denoted by the same references.

The trigger portion of the switch—that is to say the sleeve 10—is preferably made from plastic which can easily slide on the tube 6 which preferably comprises aluminum and which has an anodized surface. The round inside diameter of the sleeve 10 including the integrated ring magnet 26 is of a stepless smooth configuration so that the sleeve 10 can be easily entirely withdrawn from the tube after removal of the curved light exit window 7 which in this embodiment is only magnetically held in place (see also FIG. 1).

Unlike the situation in FIG. 2, in FIG. 3 fixing of the displaceable sleeve 10 on the tube 6 of the optical waveguide is effected not by a spiral spring but by a second annular permanent magnet 29 which is of a smaller outside diameter than the first annular permanent magnet 26 and which is mounted in the interior of the rotatable tube 6 concentrically with respect to the first magnet 26 and fixedly on the rigid end portion of the optical waveguide 2. The outside diameter of the stationary annular magnet 29 is smaller than the inside diameter of the tube 6 so that the tube 6 can still rotate freely on its rotary mounting 30.

The permanent magnet rings 26 and 29 are both poled in the direction of the axis of their ring configuration and upon assembly are mounted in such an orientation that attraction prevails between the magnet ring 26 which is advanced in the direction of the reed contact 27 and the magnet ring 29 which is disposed more at the distal end of the optical waveguide. With that arrangement of the magnet rings 26 and 29, that automatically affords a defined rest position in respect of the slidable sleeve 10 on the tube 6, similarly to that shown in FIG. 3, in which respect the two magnet rings 26, 29 are displaced somewhat relative to each in the rest or initial condition of the sleeve 10.

If the sliding sleeve 10 and therewith the magnet ring 26 are displaced in the direction of the reed switch 27 with only a light finger pressure—in which respect just a few millimeters of sliding displacement are sufficient—the reed switch 27 is activated and thus the switching operation is triggered off in the lamp device (not shown here). The attraction between the magnet rings 26 and 29 through the non-magnetic aluminum tube 6 provides that, after being released, the sleeve 10 quickly moves back into its initial position of its own accord.

The magnetic return coupling of the slidable sleeve 10 has the following further advantages over return coupling of the sleeve 10 with spring force in accordance with the first embodiment described above:

1. As magnetic attraction forces are at the greatest at the minimum distance of the two permanent magnet rings from each other and rapidly decrease upon a further increase in distance—entirely in contrast to elongation or compression of a coil spring—, this arrangement affords a kind of switching threshold, similarly to the situation with a mechanical light switch. That reduces the risk of unintentional switching procedures being implemented.

2. As both the tube 6 and also the inside surface of the sleeve 10 have completely smooth and homogenous surfaces and as moreover the sleeve 10 with the magnet ring 26 integrated therein can be easily completely stripped off the tube 6 and equally easily pushed back onto it again, the conditions are such as to be ideally suited to the hygiene demands in terms of dental operations. Both the tube 6 and also the stripped-off sleeve 10 can be easily cleaned, in which respect it is also possible to use liquid disinfectants.

3. In the case of flexible optical waveguides with a fully rotatable tube 6, the light pulse can be comfortably triggered off with the magnet hand switch according to the invention, in any desired rotational position of the tube 6.

In terms of practical operation, it may be appropriate for elongation of the slidable sleeve 10 in the direction of the reed switch 27 to be limited by a stopper ring 31 disposed on the tube 6 in the proximity of the reed switch 27, which however does not adversely affect the hygiene conditions.

For the sake of completeness it should also be mentioned that the two rings 26 and 29 do not necessarily have to be permanent magnets. One of the rings can comprise magnetizable material, for example magnetizable steel or iron.

The embodiment of the hand switch with magnet return force as shown in FIG. 3 also provides that full rotatability of the tube 6 is retained, and the advantages already referred to in this respect apply.

Figure 3A:
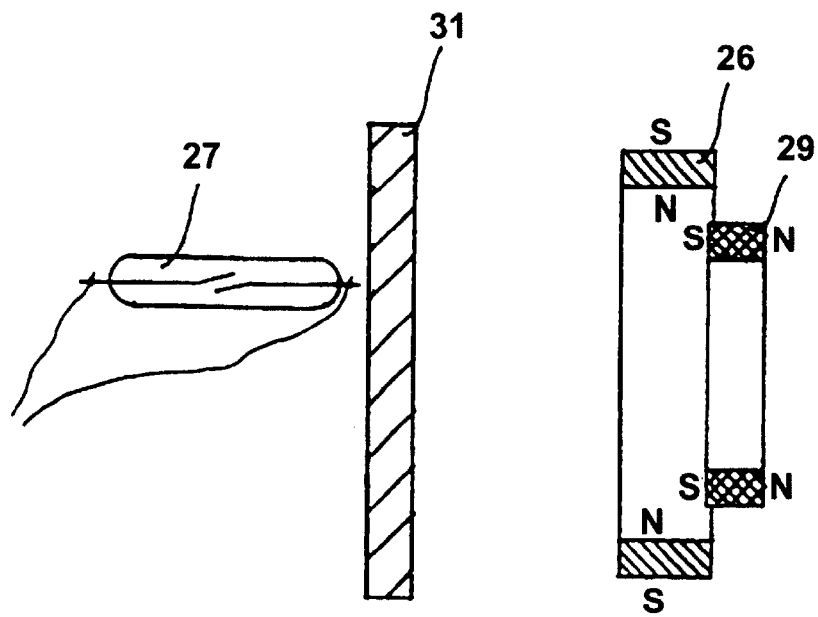
FIG. 3a shows the initial and the switched position of the magnets of the hand switch shown in FIG. 3 when it is a magnetic elastic switch.
Figure 3A:
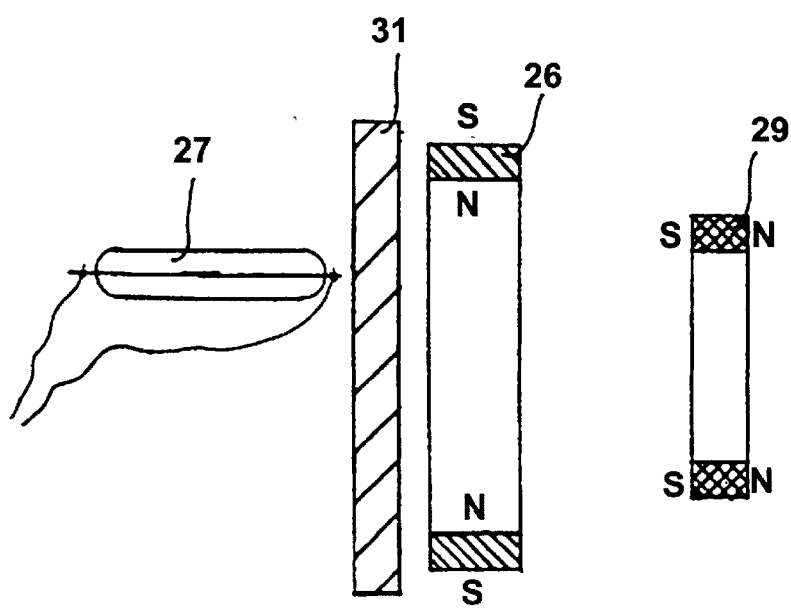

It has already been pointed out that a defined initial position for the sleeve 10 occurs, of its own accord, if attraction obtains between the magnet ring 26 which is advanced in the direction of the reed switch 27, and the fixed magnet ring 29 (that is to say in the deflected position). The condition of attraction is satisfied in a large number of situation configurations—depending on the nature and the vectorial orientation of the polarization of the annular magnets 26 and 29. FIG. 3a shows a situation in which the fixed magnet 29 is axially polarized (in which respect the north pole N is to the right in the drawing and the south pole S is to the left), whereas the displaceable magnet 26 is radially polarized (wherein the south pole S is on the outside and the north pole N is on the inside). The upper part of the Figure shows the rest or initial position of the magnet arrangement. The north poles N of the magnet 26 and the south poles S of the magnet 29 attract each other so as to ensure a positionally stable initial condition. If the magnet 26 is displaced towards the left (see the lower part of the Figure) that attraction still continues and the displaced magnet 26 still seeks to attain its rest position. If it is abruptly released it moves rapidly back. That affords a so-called "elastic magnet switch", wherein the term "elastic" is intended to express the endeavor on the part of the displaced magnet 26 to move back into the rest position.

Table 1 shows all situational configurations in terms of polarization, which give an elastic magnet switch, more specifically both having regard to axial and also radial polarization.

TABLE 1

| Polarizations which give an elastic magnetic switch | | |
|---|---|---|
| Case | Displaced magnet ring 26 | Magnet ring 29 |
| 1 | axial N–S | axial N–S |
| 2 | axial N–S | radial $N_o$, $S_i$ |
| 3 | radial $N_o$, $S_i$ | axial N–S |
| 4 | radial $N_o$, $S_i$ | radial $N_o$, $S_i$ |

Explanation:

axial polarizations are to be read from left to right, that is to say "axial N-S" means that the north pole N is arranged to the left and the south pole S is arranged to the right; and in the case of radial polarizations the indices "o" and "i" denote "outer" and "inner" respectively.

Besides the four configurations shown in Table 1, there also exist four respective equivalent configurations in which all poles N and S are interchanged. The configuration shown in FIG. 3a is equivalent to case 3, that is to say in the Figure the south pole S of the radially polarized displaced magnet ring 26 is outside and its north pole N is inside, whereas the north pole N of the axially polarized fixed magnet ring 29 is to the right and its south pole S is to the left.

Further advantageous modifications of the elastic magnet switch shown in FIGS. 3 and 3a are afforded by the measures described hereinafter.

Instead of a reed switch 27, it is also possible to mount in series in the interior of the tube 6 two or more reed switches.

With both reed switches being soldered to the wires 41, 42. Preferably the two reed switches are then arranged at the same position with respect to the axis of the rotatable tube 6, but displaced relative to each through 180°. The use of two series-connected reed switches enhances the security and reliability of the hand switch if the reeds remain sticking to each other, in the case of one reed contact.

The plastic Delrin® has proven itself as the material for the sleeve 10, by virtue of its good sliding property.

One of the two permanent magnet rings, for example the magnet ring 26, can be polarized radially but the fixed magnet ring 29 is polarized axially. That affords a somewhat longer displacement travel for the sleeve 10 until triggering of the switching operation occurs, as well as variability in terms of the magnetic return force.

In a particularly preferred embodiment therefore the rotatable tube 6 of the liquid optical waveguide includes a total of three permanent magnet rings. The first and foremost distal magnet ring 8 holds the curved applicator portion 7 which is received by a magnetizable high-quality steel sleeve 7b. The magnet ring 8 is axially polarized. The second permanent magnet ring 29 is mounted coaxially with respect to the magnet ring 8 and coaxially with respect to the axis of the cylindrical rotatable tube 6, but within the tube 6 and spaced therefrom. Its magnetic polarization is also axial, but such that like magnetic poles of the rings 8 and 29 are disposed in directly opposite relationship. The third permanent magnet ring 26 encloses the rotatable tube 6 and is also arranged coaxially with respect to the rotatable tube 6. In contrast to the magnet rings 8 and 29 however the magnet ring 26 is polarized radially. The magnet ring 26 is displaceable along the axis of the tube 6 and experiences a return force upon deflection in the direction of the reed switch 27 by virtue of the inner magnet ring 29. The stopper ring 31 which is integrated on the tube 6 limits deflection of the magnet ring 26 which is disposed in the sleeve 10. As soon as the magnet ring 26 is at a distance of between about 1 and 5 mm relative to the stopper ring, the reed switch 27—which is so arranged between the optical waveguide 2 and the tube 6 that it is sufficiently spaced from all three magnet rings 8, 26 and 29—closes so that it is switched open in the rest position of the sleeve 10. Switching deflection of the sleeve 10 or the magnet ring 26 is between about 5 and 10 mm.

With that arrangement of the magnet rings 26 and 29, the assembly of its own accord affords a defined rest position for the sliding sleeve 10 on the tube 6, similarly to the situation shown in FIG. 3, while in the rest or initial position of the sliding sleeve 10 the two magnet rings 26, 29 are somewhat displaced relative to each.

Besides the possibility already referred to above, that one of the annular magnets 26 or 29 is not in the form of a permanent magnet but comprises magnetizable material (for example magnetizable steel or iron), it should also be mentioned that, instead of the permanent magnet rings, it is also possible to use ring structures which are composed of a plurality of sectors arranged in a circular configuration around the axis of the rotatable tube 6. Individual permanent magnets or magnetizable materials can be used as the magnetizable material. Magnetic foils or sheets which are bent or curved into a circular configuration are also suitable.

Instead of a reed switch 27 it is also possible to use a magnetically activatable Hall switch which requires an electrical auxiliary voltage and therefore also at least three feed wires.

If, for reasons of ergonomy of the optical waveguide with hand switch, it is desired that the sleeve 10 is positioned entirely distally—that is to say on the tube 6 as far as possible at the light exit end—, the inner holding magnet ring 29 can be omitted. In that case the permanent magnet ring 8 (see also FIG. 1), in addition to its function of holding the curved applicator portion 7 in place, also takes over the function of providing for magnetic positioning and the return action for the sleeve 10 with integrated ring magnet 26.

The described elastic switch can be converted into a so-called "magnetic flip switch", by inversion of polarization in each situational configuration.

In the case of a magnetic flip switch according to the invention, the displaceable magnet has a stable initial position and a stable switched position. The flip switch is formed by the co-operation of the displaceable magnet with a second annular magnet which is arranged in the interior of the rotatable tube coaxially with respect to the displaceable magnet and fixedly on the liquid optical waveguide. If the displaceable magnet is moved into a position such that it is over the fixed magnet (that is possible because it is of a larger diameter and bears on the outside against the rotatable tube), then—again in dependence on the nature and the vectorial orientation of polarization of the annular magnets 26 and 29 —there are configurations in which the fixed magnet so-to-speak "captures" the displaceable magnet and a stable initial position of the displaceable magnet comes about, in which the magnetic forces are in a condition of metastable equilibrium. If at the same time the magnets are so oriented that repulsion obtains between the fixed magnet 29 and the movable magnet 26 which is displaced in the direction of the magnetically activatable switch, then the displaceable magnet is repelled after the condition of metastable equilibrium is overcome, that is to say, it moves away from the fixed magnet. If its movement options are limited in such a way that it is fixed in a position in which the magnetically activatable switch remains permanently switched on, that affords a stable switched position. In accordance with a preferred embodiment of the magnetic flip switch the stable switched position of the displaceable magnet is formed by a stopper ring which limits the displaceability of the magnet in a direction towards the magnetically activatable switch. Preferably the displaceable magnet is disposed in the interior of the sleeve which surrounds the rotatable tube and is axially displaceable thereon.

Table 2 shows all situational configurations in terms of polarization, which afford a magnetic flip switch, once again having regard to both axial and also radial polarization.

TABLE 2

| Polarizations which give an magnetic flip switch | | |
|---|---|---|
| Case | Displaced magnet ring 26 | Magnet ring 29 |
| 1 | axial N–S | axial S–N |
| 2 | axial N–S | radial $S_o$, $N_i$ |
| 3 | radial $N_o$, $S_i$ | axial S–N |
| 4 | radial $N_o$, $S_i$ | radial $S_o$, $N_i$ |

Explanation:

axial polarizations are to be read from left to right, that is to say "axial N-S" means that the north pole N is arranged to the left and the south pole S is arranged to the right; and in the case of radial polarizations the indices "o" and "i" denote "outer" and "inner" respectively.

Figure 3B:
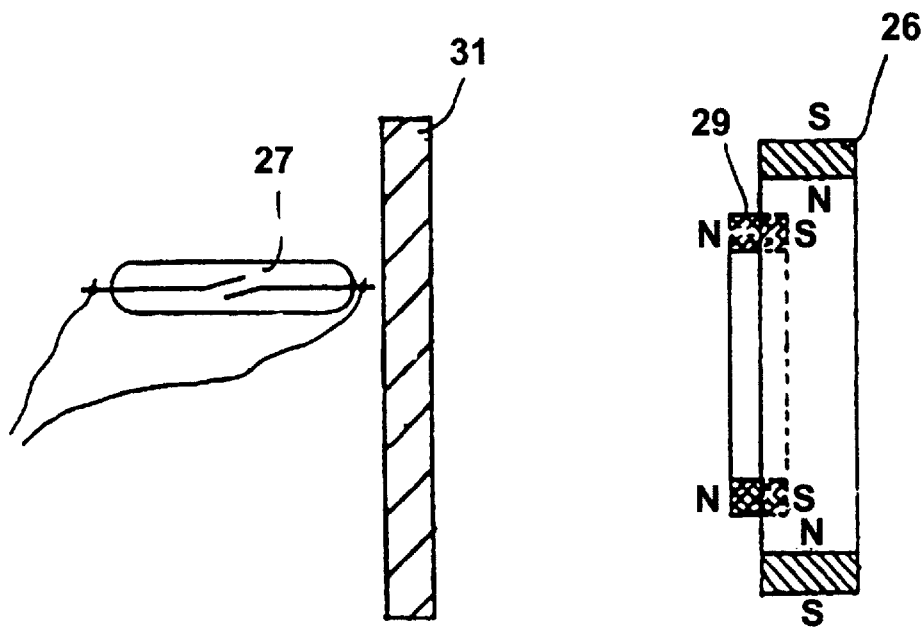
FIG. 3b shows the initial and the switched position of the magnets of the hand switch shown in FIG. 3, when it is a magnetic snap or flip switch.
Figure 3B:
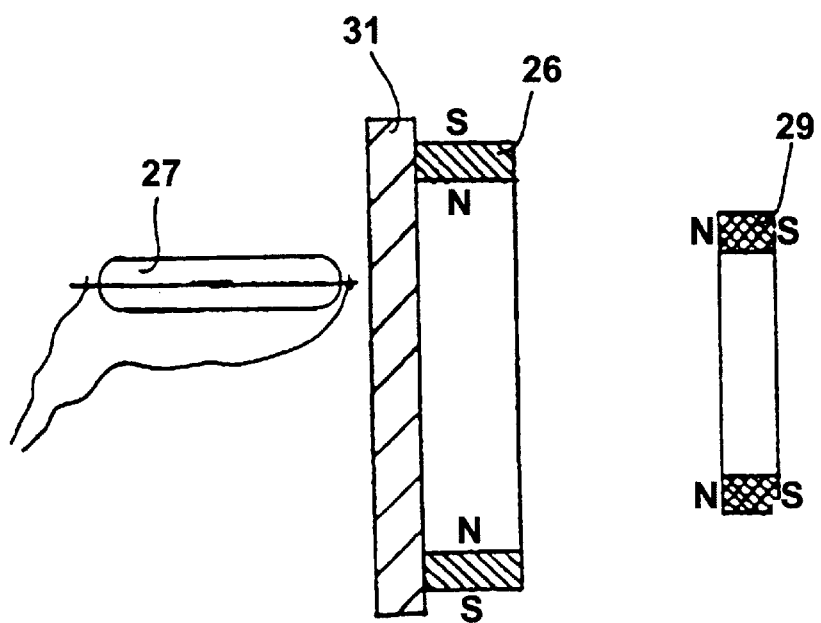

There also exist four respective equivalent configurations in which all poles S and N are interchanged. The configuration shown in FIG. 3b is equivalent to case 3 in Table 2. The upper part of the Figure again shows the stable initial position which is implemented here by a metastable equilibrium of forces. The displaceable magnet 26 is radially polarized, with the south pole S being on the outside and the north pole N on the inside. In contrast the fixed magnet 29 is polarized axially, with the south pole S being to the right and the north pole N to the left. In the initial position the south pole S of the fixed magnet 29, which is at the right, and the inwardly disposed north pole N of the displaceable magnet 26 attract each other so that the magnet arrangement is positionally stable. The equilibrium of forces is however metastable because, upon displacement of the magnet 26 towards the left, the repulsion forces between the north pole N of the fixed magnet 29, which points towards the left, and the inwardly disposed north pole N of the radially polarized, displaced magnet 26 steadily increase. If therefore the magnet 26 is displaced beyond a certain point, forces occur which move the system further out of the old condition of equilibrium, that is to say, the repulsion forces gain the upper hand and move the magnet 26 of its own accord further towards the left. In the Figure, the stopper ring 31 provides that displaceability of the magnet 26 in a direction towards the magnetically activatable switch 27 is limited. It thus remains in a position in which the reed switch 27 is permanently switched on.

Another magnetic flip switch for the optical waveguide according to the invention is afforded by an arrangement of three mutually coaxial annular magnets which also form a stable initial position and a stable switched position. This magnet arrangement includes two interconnected terminal magnets and a centrally disposed magnet, wherein the centrally disposed magnet and the terminal magnets are displaceable over each other in such a way that the centrally disposed magnet is arranged between the terminal magnets. In that condition there are once again situational configurations in which the magnets so-to-speak "capture" each other and a stable initial position for the magnet arrangement occurs, in which magnetic forces are in metastable equilibrium.

To produce the stable switched position of the switch the magnets are movable in such a way that either the centrally disposed magnet is stationary and the terminal magnets are displaceable relative thereto and by such a distance that they are stably positioned between the magnetically activatable switch and the centrally disposed magnet. Alternatively, the terminal magnets can be stationary and the centrally disposed magnet can be displaceable relative thereto and by such a distance that it is stably positioned between the magnetically activatable switch and one of the terminal magnets. In order to achieve such displaceability, either the terminal magnets are axially displaceable on the rotatable tube and the centrally disposed magnet is fixedly arranged on the optical waveguide, or the centrally disposed magnet is axially displaceable on the rotatable tube and the terminal magnets are fixedly arranged on the optical waveguide. The possibility of the magnets being moved one over the other is afforded by virtue of their different diameters.

Optionally, the displaceable magnet or magnets can be arranged in the displaceable sleeve.

The advantages of the described magnetic flip switch (this applies equally in regard to the embodiment of FIG. 3b and the flip switch described herein with three magnets) are on the one hand that a higher level of resistance has to be overcome upon deflection in the direction of the magnetic switch. In addition, flip switches do not independently move rapidly back into the initial position but remain in their stable switched position. In order to trigger off a fresh light pulse, the sleeve 10 first has to be moved back again into the initial position and, in so doing, overcome once again a certain—so-to-speak mechanical—resistance. That switching characteristic provides that an unintended light pulse which would dazzle the patient is not so easily triggered off.

Figure 4:
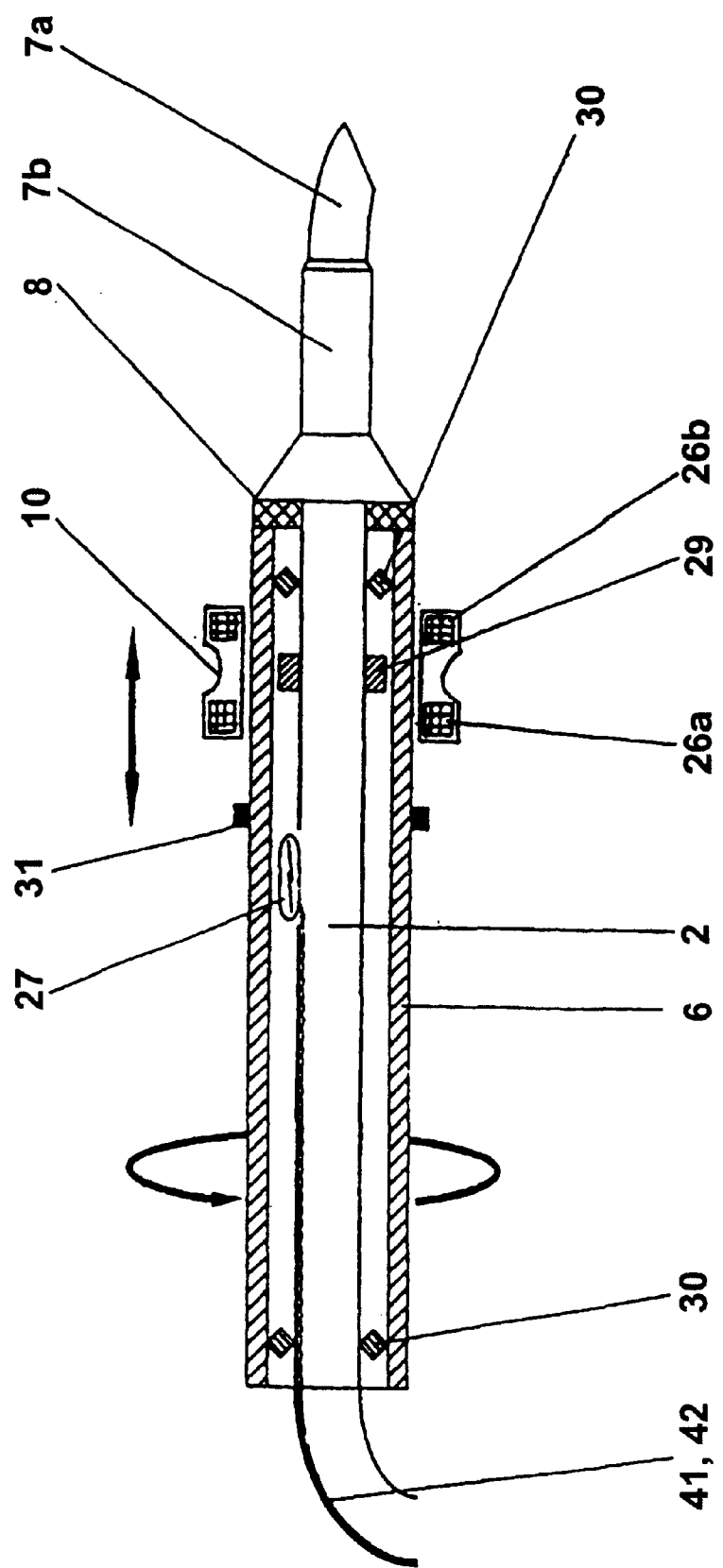
FIG. 4 shows a liquid optical waveguide according to the invention having a hand switch which has an arrangement with three magnets.

An embodiment in accordance with the first foregoing alternative is shown in FIG. 4. It substantially corresponds to FIG. 3, but as a departure therefrom the sleeve 10 has not one but two mutually spaced and coaxially arranged annular magnets 26a and 26b; these form the terminal magnets. The annular magnet 29 is unchanged in comparison with FIG. 3 and forms the centrally disposed magnet. It performs the double function of a return and holding magnet. In the initial position as illustrated the sleeve 10 is so positioned that the centrally disposed magnet 29 is arranged substantially centrally between the terminal magnets 26a and 26b. Like poles of the magnets 29 and 8 are disposed in mutually opposite relationship.

The attainment of a stable initial position has already been described with reference to FIG. 3b; corresponding considerations apply in regard to the arrangement having three magnets. For the attainment of a stable switched position however it is not absolutely necessary to limit the displaceability of the displaced magnets 26a and 26b. More specifically, there are situational configurations in terms of polarization, in which the right-hand terminal magnet 26b is attracted by the centrally disposed magnet 29, in the switched position. By virtue of that attraction it then remains stably in the switched position, without any need for limiting the movement thereof, in the form of a stopper ring 31. It is only if it is repelled by the centrally disposed magnet 29 that it is necessary to provide a limitation effect.

Figure 4A:
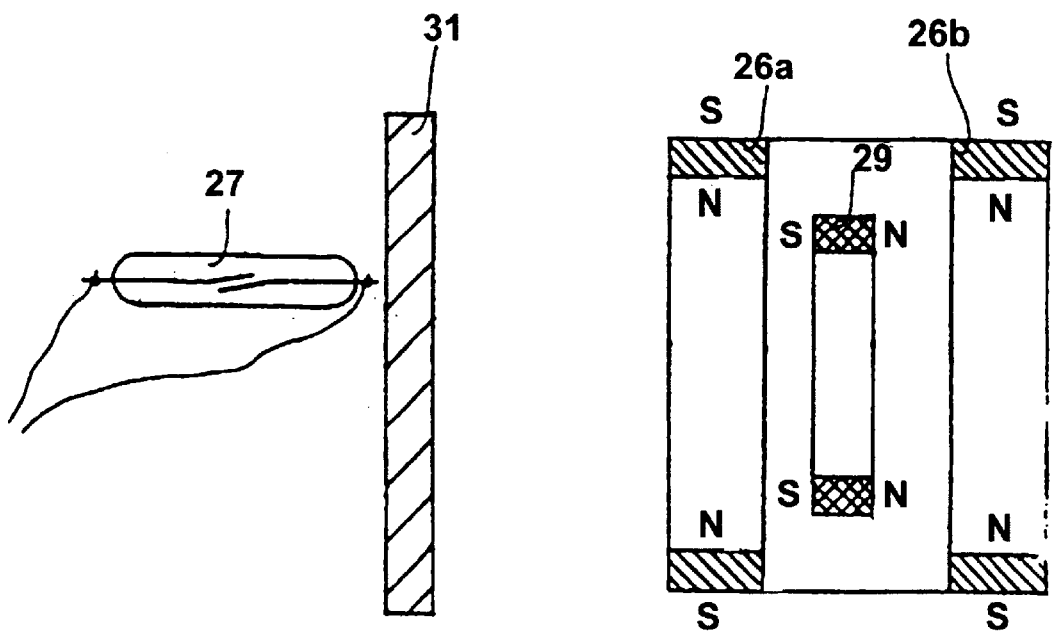
FIG. 4a shows the initial and the switched position of the magnets of the hand switch shown in FIG. 4.
Figure 4A:
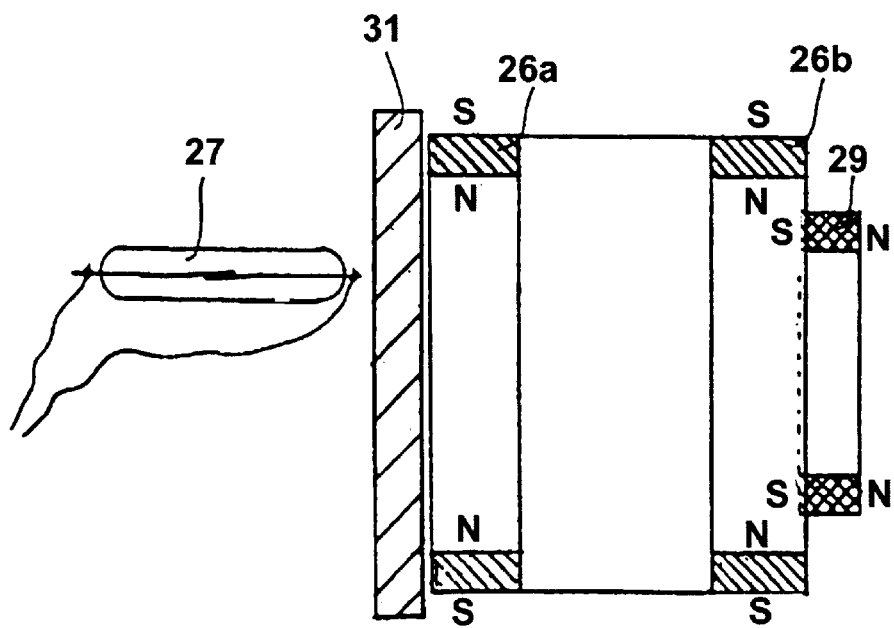

Details in this respect are to be found in the diagrammatic view of FIG. 4a. This corresponds to the embodiment of FIG. 4, wherein there are provided a fixed annular magnet 29 involving axial polarization and two displaceable annular magnets 26a and 26b involving radial polarization; the latter form the terminal magnets. The upper part of FIG. 4a shows the arrangement of the magnets in the initial position. Similarly to the situation shown in FIG. 3b, their position relative to each is stable because the north pole N of the axially polarized magnet 29 and the north pole N of the radially polarized magnet 26b mutually repel. On the other hand the south pole S of the axially polarized magnet 29 and the north pole N of the radially polarized magnet 26a mutually attract.

If the terminal annular magnets 26a and 26b are displaced together towards the left in the drawing, it is firstly necessary to overcome a resistance which occurs due to repulsion of the north pole N of the axially polarized magnet 29 with the north pole N of the radially polarized magnet 26b. After the resistance has been overcome the arrangement of the magnets reaches the switched position in which it stably remains because the north pole N of the radially polarized magnet 26b and the south pole S of the axially polarized magnet 29 mutually attract. That therefore affords a stable switched position, even without movement limitation. That constitutes a particular advantage of this embodiment of the magnetic flip switch with three magnets.

Figure 5:
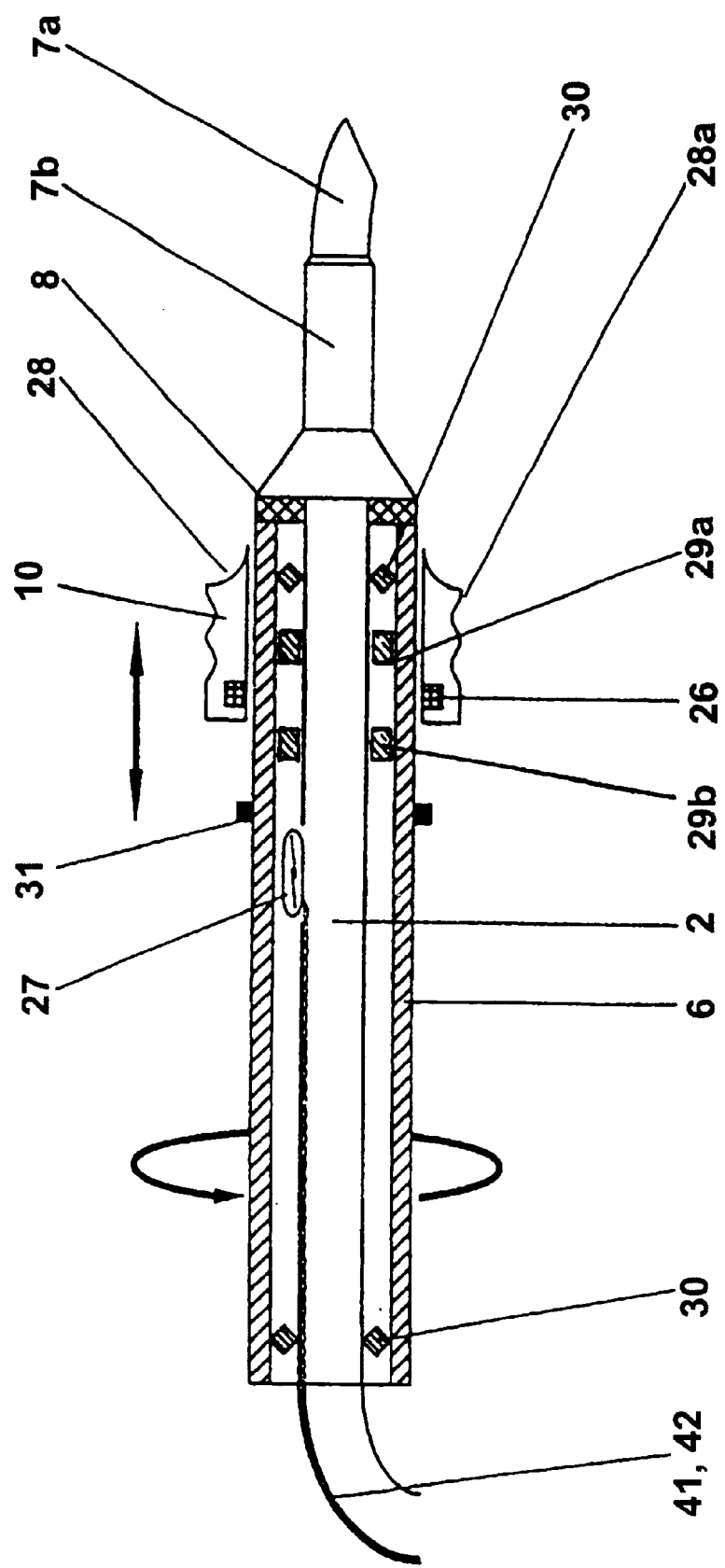
FIG. 5 shows a modification of the hand switch of the liquid optical waveguide of FIG. 4.

An embodiment in accordance with the second above alternative is shown in FIG. 5. Here, the sleeve 10 with the magnet 26 (which here is polarized radially) is of the configuration as shown in FIG. 3, with the magnet 26 forming the centrally disposed magnet. The magnet 29 in FIG. 3 however is divided into two spaced magnets 29a and 29b (axially polarized in this case) which form the terminal magnets.

The embodiment of FIG. 5 is less preferred than that of FIG. 4. The advantage of the hand switch in FIG. 4 is that it can be operated selectively as an arrangement with two or with three magnets, insofar as either the sleeve of FIG. 3 (one magnet) or that of FIG. 4 (two magnets) is pushed over the rotatable tube 6 and it is just thereby—that is to say without further structural involvement—that the differing switching characteristics are obtained. In the case of the hand switch in FIG. 5 in contrast the interior of the optical waveguide 2 would have to be modified.

At the present time the most preferred embodiment is the embodiment of the optical waveguide according to the invention as shown in FIG. 3. A practical configuration by way of example thereof is specified as follows in terms of its material, dimensions and magnetic data. The annular magnet 29 is axially polarized, with the north pole being towards the distal end of the optical waveguide. The magnet itself comprises neodymium/iron/boron sintered material, it is of a thickness of 2.5 mm, an outside diameter of 11.7 mm and an inside diameter of 9.1 mm. The annular magnet 26 arranged in the sleeve 10 is radially polarized, with the south pole being disposed outwardly and the north pole inwardly. It comprises plastic-bound neodymium/iron/boron material, and it is of a thickness of 4 mm, an outside diameter of 18 mm and an inside diameter of 15 mm. The rotatable tube 6 comprises aluminum and involves the dimensions $Ø_o=14$ mm, $Ø_i=12$ mm and l=130 mm. The stopper ring 31 is disposed at a spacing of about 15 mm from the inner annular magnet 29. The magnetically activatable switch 27 is a reed switch 27 and involves the dimensions l=11 mm and d=2.1 mm; its sensitivity is in the range of between 10 and 25 ampere turns.

A practical embodiment of the—similarly preferred—optical waveguide according to the invention as shown in FIG. 4 is of the following specification. The two annular magnets 26a and 26b and the annular magnet 29 are of the specification as set forth above in relation to FIG. 3. The magnets 26a and 26b are arranged in the sleeve 10 at a spacing of between about 3 and 10 mm relative to each. The position of the stopper ring 31, the annular magnet 29 and the reed switch 27 are also specified as described hereinbefore in relation to FIG. 3; that also applies in regard to their materials and dimensions.

In a practical embodiment of a—less preferred—optical waveguide according to the invention as illustrated in FIG. 5 the specifications of the annular magnets 29a and 29b are identical to that of the annular magnet 29 in FIG. 3. The magnets 29a and 29b are distally arranged in coaxial relationship with the axis of the optical waveguide 2 but only spaced from each other by a few mm, with like magnetic poles being in mutually opposite relationship.

FIGS. 6, 7, 8 and 9 which are described hereinafter show configurations of a liquid optical waveguide with a hand switch, in which the hand switch is in the form of a pistol grip or a grip portion.

Figure 6:
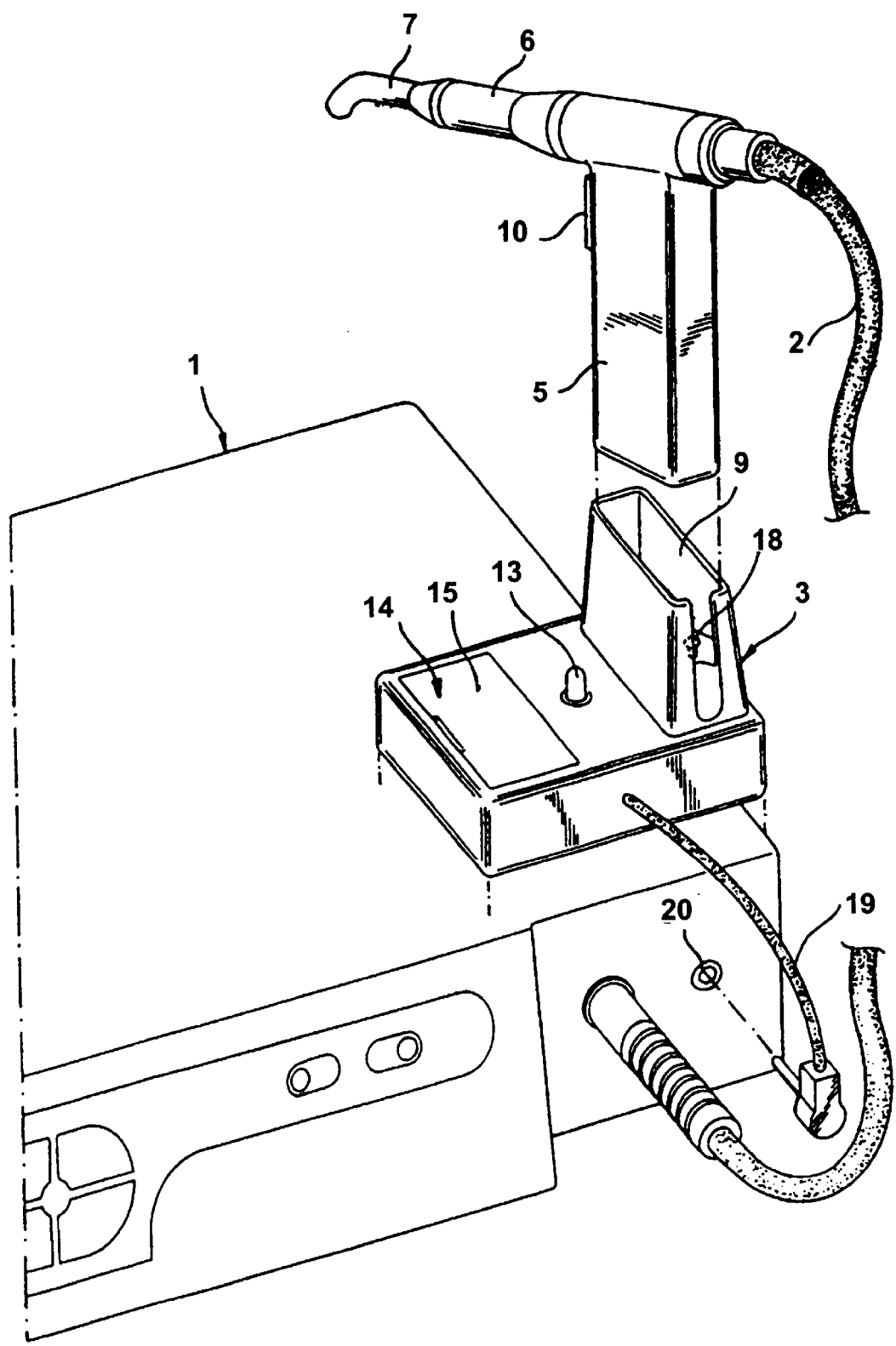
FIG. 6 shows an optical waveguide with a hand switch in the form of a pistol grip.

FIG. 6 shows the structure of the hand switch according to the invention for dental liquid optical waveguides in conjunction with a lamp housing 1 (not described in greater detail herein) to which the optical waveguide 2 is optically coupled. A crucial aspect is mounting of a grip 5 with trigger 10 to the rotatable hand tube 6, wherein the grip 5 is fixed on the tube 6 so that full rotatability of the tube 6 is maintained. Equally maintained is the magnetic and thus rotatable coupling of the curved applicator window 7 to the tube 6, as already described with reference to FIG. 1.

By virtue of the hand grip 5 being mounted to the elongate tube 6 in a substantially right-angled configuration, as shown in FIG. 6, the pencil-like handpiece is converted into a pistol-like handpiece, which affords an ergonomic improvement in terms of manipulation of the optical waveguide, having regard to the low level of flexibility of the liquid optical waveguide and the resulting lever action on the handpiece.

Figure 7:
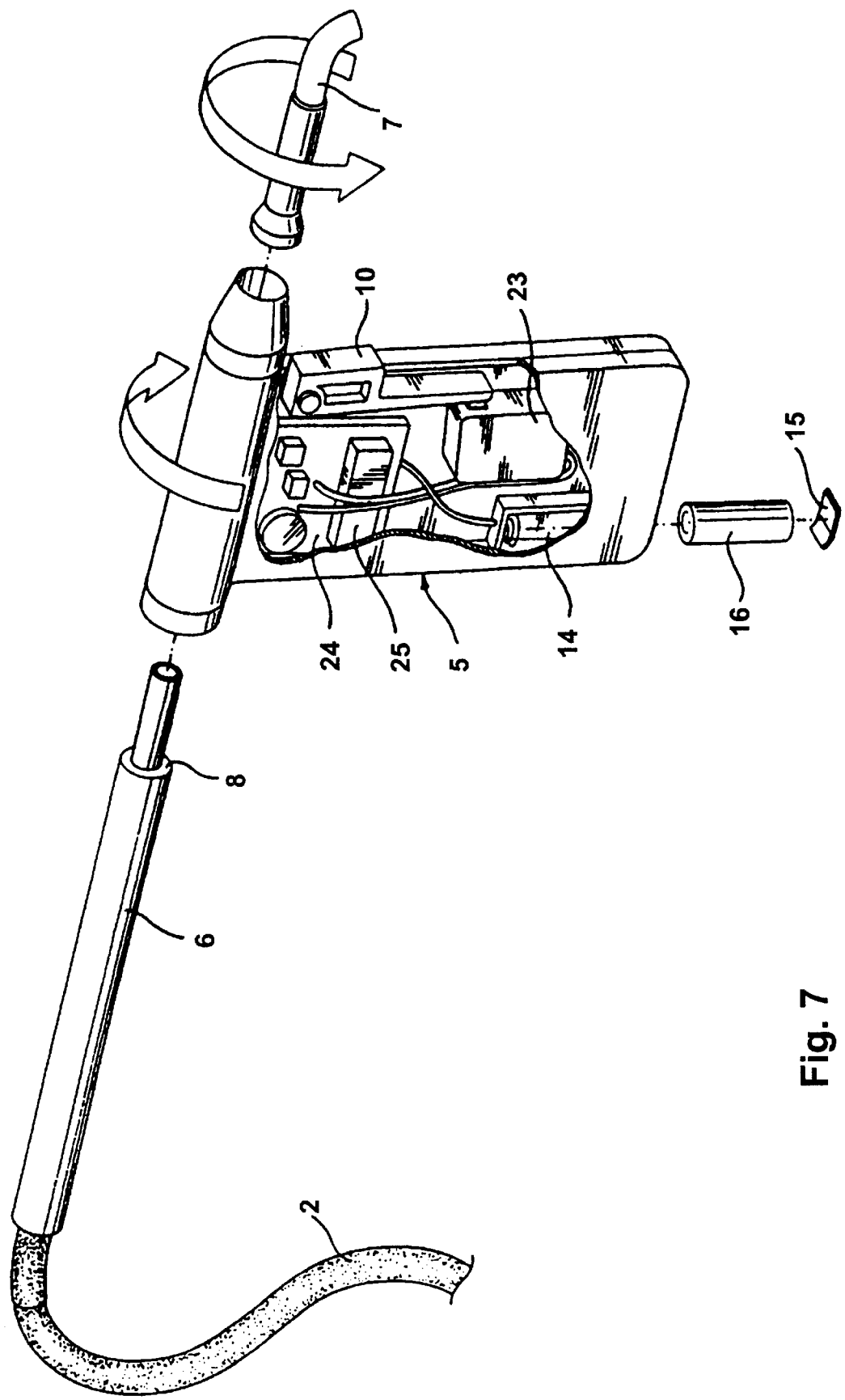
FIG. 7 is a view of the switching elements of the hand switch of FIG. 6.

It will be apparent from looking at FIG. 7 how the pistol grip 5 which is hollow in its interior affords sufficient space to be able to comfortably incorporate therein a mechanical switch 23 which can be activated by the trigger 10 and which in turn triggers off a high frequency pulse of a wireless miniature transmitter 24 which can also be easily disposed in the pistol grip, including a small dry battery 16 which provides the power supply for the miniature transmitter 24.

Installation of the electronics in the interior of the pistol grip 5 is shown in FIG. 7 in which the various components 6, 5 and 7 of the handpiece with pistol grip are separated from each other for reasons of enhanced clarity of the drawing. The dry battery 16 is held in the battery holder 14 and can be easily replaced by opening the closure cover 15. The core part of the transmitter 24 is a chip 25 which permits encoding in the form of amplitude modulation of the emitted high frequency pulse.

The pistol grip 5 is desirably composed of two internally hollow symmetrical half-shell portions so that there is sufficient space in the interior of the half-shell portions for the installation of a mass-production transmitter circuit board 24 with switch 23 and dry battery 14, similarly as are used in large numbers in motor vehicles for opening the doors, switching on the lights etc., which keeps down the costs of the transmitter. As no conductor wires have to be fitted into the optical waveguide for radio control, the pistol grip equipped with transmitter can be mounted on liquid optical waveguides which are already in dental use, by virtue of it being pushed over the standardized rotatable tube 6 and then fixed in position.

Full rotatability of the tube 6 with pistol grip mounted thereon is retained and that therefore affords optimum manipulatability for the dentist. The pistol grip 5 with trigger 10 and installed transmitter 24 can be easily pushed over the tube 6, that is to say however that the many optical waveguides which are already in existence for hand switch operation can be subsequently fitted therewith. The same applies in regard to the receiver module 3 which is shown in FIG. 6 and which is combined with a storage device 9 for the pistol grip and in the interior of which are disposed the receiver circuit board which is tuned to the encoding of the transmitter, with antenna, together with a dry battery. The battery in the receiver module is replaceable by removal of the battery compartment 14-cover 15, the light emitting diode 13 indicating standby operation of the receiver. When, after termination of the polymerization operation, the pistol-shaped handpiece 5 is put back into the storage device 9, then the standby current of the receiver is switched off by way of the contact switch 18 disposed in the bottom of the storage device 9, in which case the light emitting diode 13 goes out, which considerably prolongs the operating life of the battery. The contact switch 18 can also be in the form of a magnetic switch, in such a way that disposed in the interior of the pistol grip 5 is a permanent magnet which, when the pistol is set down, actuates a reed relay.

The receiver module 3 is a unit which is detached from the lamp housing 1, in which case contact is made by way of the jack socket 20 on the lamp housing 1 only with the wire 19 from the receiver module. The jack socket 20 is on the apparatus 1 the input socket for the foot switch (not shown here) which is replaced here by the hand switch according to the invention with radio control. The receiver connected by way of wires 19 to the socket 20 triggers an electrical closing operation upon actuation by the transmitter and thus acts similarly to the replaced foot switch which has a mechanical action.

That therefore means that the polymerization apparatuses which are already wide-spread in large numbers in dental practice can be subsequently fitted with the hand switch according to the invention with radio remote control, without the need to make any modification either on the optical waveguide or on the lamp box. It will be appreciated that in the case of newly designed apparatuses the receiver module can be integrated in the light box 1, in which case then the power supply is desirably effected not by means of a battery but by branching from the power supply for the lamp. As the distance to be covered by the radio control is at a maximum only a few meters (the maximum length of the optical waveguides is 3 m) the transmitter can easily manage with a transmission power in the range of between 1 and 10 mW. In actual fact the transmission power is under one milliwatt so that the transmitter falls into the category "LPD", that is to say "Low Power Device". That fact considerably facilitates practical implementation of the hand switch according to the invention.

Figure 8:
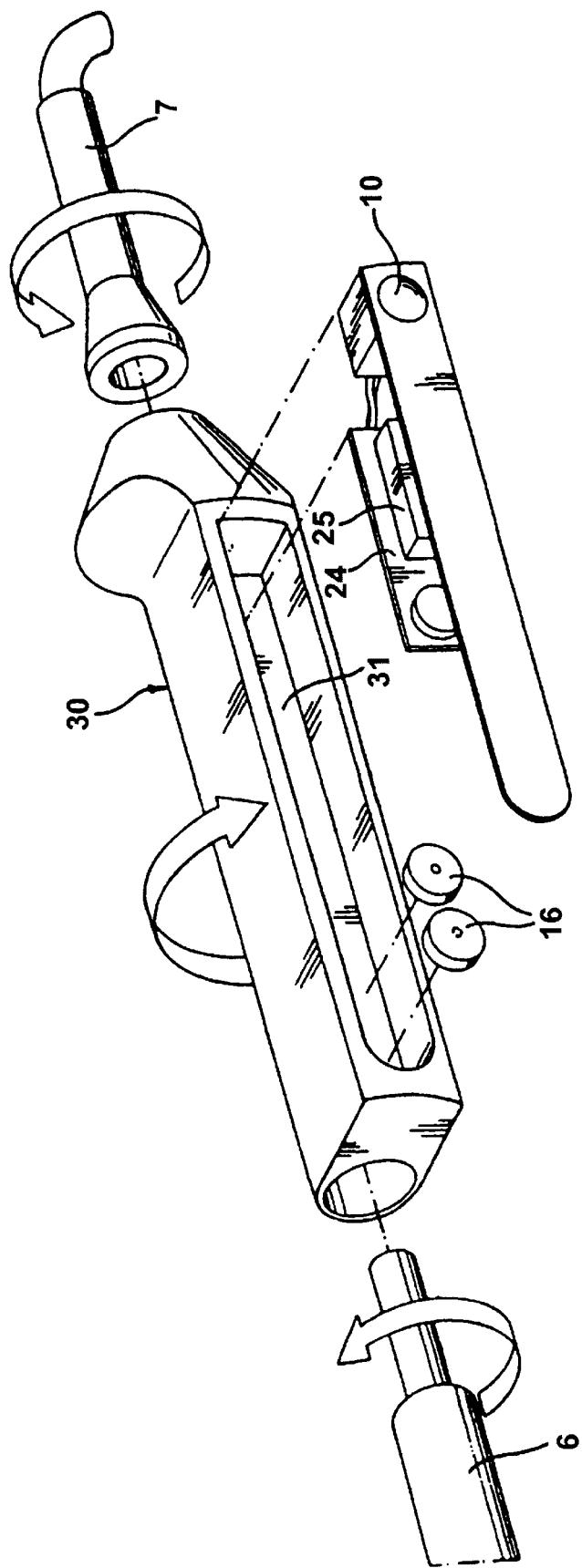
FIG. 8 shows a modification of the hand switch of FIG. 7a, and FIG. 9 shows a modification of the hand switch of FIG. 6.

Although the pistol grip 5 with trigger 10, which is fixed on the rotatable tube 6, represents an ergonomically optimum solution in terms of handling of the liquid optical waveguide by the dentist when irradiating fillings, an alternative option in terms of installation of a miniature transmitter in an elongate, fully rotatable grip portion 32 should also be illustrated here with reference to FIG. 8, for the sake of completeness, which still allows the dentist the usual manner of handling the liquid optical waveguide without hand switch, as shown in FIG. 1, in accordance with the previous state of the art, so that there is no need for any change in terms of handling, as required by the pistol grip.

The elongate grip portion 32 which is virtually of an oval shape in cross-section has a bore 32 which passes along the entire longitudinal axis and which is displaced towards the edge, for the accurate insertion of the rotatable hand tube 6. The grip portion 32 can be fixedly connected to the rotatable tube 6 but it can itself be mounted fully rotatably instead of the tube 6 on the rigid end portion of the optical waveguide 2. The grip portion 32 has a milled-out trough or recess 31 in which the transmitter circuit board 24 with encoding chip 25 is disposed. Also disposed in the recess 31 are the button cells 16 for the power supply for the transmitter. The transmitter is activated with the index finger by means of the switch 10. Adjoining the light exit end of the grip portion is the curved applicator window 7, once again held rotatably by a magnet ring 8. The receiver module remains unchanged with this handpiece, just as described with reference to FIG. 6, but provided with a suitable storage device 9 which has not been shown here.

Mounting a handy pistol grip 5 with trigger 10 more or less at a right angle with respect to the rigid end portion of the liquid optical waveguide 2 affords such a great ergonomic advantage over the pencil-like hand tube 6 with the corresponding manner of holding it in the hand, that in regard to many uses of the liquid optical waveguide in which optimum manipulability is not so important, as for example in the case of the polymerization of industrial adhesives, it is even possible entirely to forego rotatability of the tube 6 with pistol grip 5 about the axis of the end of the optical waveguide. That means however that in such cases the pistol grip 5 can be fixed to the rigid end portion of the liquid optical waveguide 2.

The liquid optical waveguide 2 admittedly presents a considerable degree of resistance to rotation in itself, but, by virtue of the lever action of a handy pistol grip 5 which is fitted at a right angle to the end portion of the optical waveguide, that resistance is not so very noticeable from the point of view of the user, as in the case of the pencil-like handpiece. That is especially the case because in the rarest cases the user is required to implement rotational movements of up to 360° and in addition the curved applicator window 7 which is mounted only magnetically and therefore rotatably is still available to the user, whereby the applicator window can be roughly oriented by hand prior to application of the radiation dose.

Figure 9:
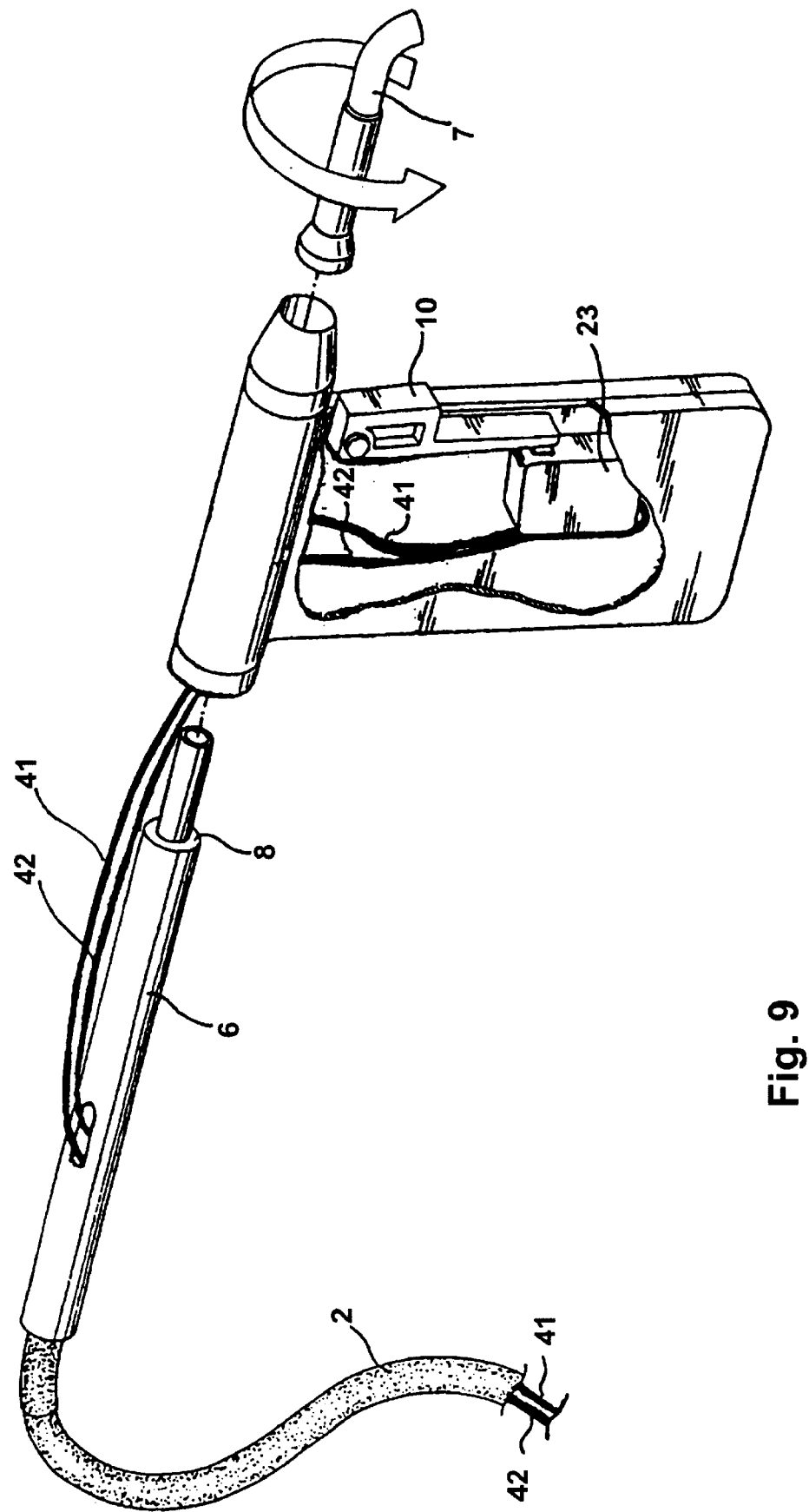

If however full rotatability of the pistol grip 5 and/or the tube 6 with pistol grip 5 about the axis of the end portion of the liquid optical waveguide is waived, that affords the possibility of providing a galvanic switch circuit with thin wires or stranded conductors which are guided in the interior of the liquid optical waveguide 2, instead of a hand switch with wireless radio control. FIG. 9 shows such an arrangement with a galvanic hand switch for a liquid optical waveguide with pistol grip which is mounted fixedly to the rigid, non-rotatable end tube 6 of the liquid optical waveguide.

Besides the trigger 10, the pistol grip 5 includes only a mechanical switch 23 from which two thin insulated wires or stranded conductors 41, 42 extend and are passed through an opening 43 into the interior of the liquid optical waveguide 2, for example into the space between the C-F polymer hoze and the metal aluminum wound hoze. The two wires 41, 42 are soldered in the pistol grip to the switch 23 and extend from there in the interior of the optical waveguide 2 to the light entry adaptor 21, see FIG. 6, and are there taken out of the optical waveguide and introduced for example with a jack plug into the receiving socket 20 in the lamp housing 1, which represents the socket for the foot switch to be replaced.

The switch 23 which can be activated by the trigger 10 short-circuits the two wires which with insulation are for example of a diameter of only 0.7 mm and which for that reason can be easily accommodated in the interior of the optical waveguide 2. The galvanic pistol grip hand switch thus acts in a similar manner to the foot switch to be replaced, namely as a closing device.

The two wires or conductors 41, 42 which extend in the interior of the liquid optical waveguide in the narrow gap-shaped space between the optical waveguide C-F hoze and the aluminum wound hoze are of a diameter with insulation <1 mm, for example 0.7 mm, and, due to the transparency of the optical waveguide hoze, are exposed to highly intensive blue or UV-radiation. That radiation originates from the scatter radiation loss of the optical waveguide. The insulation on the wires 41, 42 must be UV-resistant and therefore must not become friable as a consequence of the ongoing irradiation effect while on the other hand it is to be highly abrasion-resistant because of the friction of the wires against the aluminum hoze as a consequence of frequent bending of the optical waveguide. Conductors or wires 41, 42 which have an insulation of fluorine-bearing plastics such as for example Kynar®7 (polyvinylidene fluoride) or Teflon®7 PFA, Teflon®7 FEP or Teflon®7 PTFE, have proven themselves to be successful.

In the case of the galvanic hand switch in the pistol grip 5 it is possible to permit limited rotatability of the tube 6 to which the pistol grip 5 is fixedly mounted for example within an angular sector of ±180° about a zero or neutral position if a certain compensating length is provided for the wires 41, 42 in the pistol grip so that the solder joins of the wires 41, 42 to the switch 23 are not subjected to stresses when the pistol grip 5 with the rotary tube 6 is rotated within the angular sector which is limited to a maximum of ±180°. Limiting the rotatability of the tube 6 with fixedly connected pistol grip 5 can be effected by a mechanical abutment.

Any lamps can be included in the polymerization apparatus 1 to which the liquid optical waveguide with one of the hand switches according to the invention is coupled. The novel liquid optical waveguide with hand switch acts in a particularly advantageous fashion however in relation to the polymerization apparatus with an ultra-high-pressure mercury lamp such as the UHP-lamp from Philips (for example UHP 120W) or the VIP-lamp lamp of the same design from Osram (for example VIP 120W) which operate with an extremely high Hg-vapor operating pressure of about 200 at. Those lamps comprise the Hg-burner in a thick-wall quartz glass bulb which in turn is cemented into an elliptoidal glass body so that the plasma center of the Hg-burner is substantially coincident with the one focus of the elliptoid. The inside surface of the latter has a selective dielectric thin-layer reflective metal coating which is particularly high for dental polymerization in the range of 400 nm $<\lambda<500$ nm (R close to 100%) and which is as low as possible for wavelengths >500 nm (R near to 0%). For the polymerization of fillings in the dental sector, the spectral useful range is further limited to the wavelength range of 430 nm $<\lambda<500$ nm by additional thin-layer filters which are positioned in front of the light entry surface of the optical waveguide. For industrial polymerization the mirror coating should be such as to afford a high level of reflectivity also in the UV-range, that is to say for 250 nm $<\lambda<400$ nm.

Because of the high operating pressure of the UHP- and the VIP-lamps of about 200 at, it is appropriate for safety reasons, because of the risk of explosion of the burner, for the beam exit opening of the elliptoidal reflector to be covered over with a thick-wall (d=3 mm) transparent plane plate for example of quartz glass or Tempax®7 glass, which is cemented, glued or welded in position.

Lamp apparatuses of that kind for polymerization operations with UHP- or VIP-lamps are already described in German patent application No. 198 38 166.2. They are distinguished by an extremely high level of optical efficiency, for which reason lamps of only 120 W electrical input power from a liquid optical waveguide with a light-active core of 5 mm Ø already afford such high levels of radiation power in the U which is useful for the polymerization operation (in the watt range) that flash polymerization which lasts only about one second is possible in dentistry.

Because of the low level of electrical input power required such polymerization apparatuses with VIP7 or UHP7 lamp can be very small and can be of only low weight, which makes those apparatuses easily transportable, for example between a plurality of treatment units in a dental practice.

The availability of a hand switch at the end of the optical waveguide additionally facilitates mobile use of that polymerization apparatus because the cumbersome foot switch does not have to be repeatedly re-installed.

LIST OF REFERENCES

1 lamp housing
2 optical waveguide
3 receiver module
4 end portion
5 pistol grip, grip
6 tube
7 applicator portion
7*a* applicator window
8 magnet ring
8*a* optical waveguide end
9 storage device
10 trigger, sleeve
11
12
13 light emitting diode
14 battery holder
15 closure cover
16 battery
17
18 contact switch
19 wire
20 jack socket
21 listening adapter
22
23 switch
24 (miniature) transmitter, circuit board
24 a spiral spring
25 encoder (chip)
25 a stopper ring
26 permanent magnet ring
26*a* permanent magnet ring
26*b* permanent magnet ring
27 magnetically activatable switch
28 finger grip recess
28*a* knurling
29 permanent magnet ring
29*a* permanent magnet ring
29*b* permanent magnet ring
30 rotary mounting
31 stopper ring
32 grip portion
33
34
35
36
37
38
39
40
41 wire, stranded conductor
42 wire, stranded conductor

What is claimed is:

1. An optical waveguide (2) for an optical lighting arrangement having a tube (6) arranged at its light exit end, characterized in that the tube (6) comprises a non-magnetic material,
wherein the optical waveguide (2) has a hand switch for controlling the radiation flow of the optical lighting arrangement, said hand switch being formed by:
at least one magnetically activatable switch (27) which is arranged between the optical waveguide (2) and the tube (6) and which is disposed fixedly on the outside peripheral surface of the optical waveguide (2) and which is spaced from the inside surface of the tube (6), and
at least one annular magnet (26) which is arranged on the tube (6) and which bears snugly against the tube (6) and which is displaceable axially thereon from an initial position to a switched position in which the magnetically activatable switch (27) is actuated,
wherein extending from the magnetically activatable switch (27) are two thin wires or stranded conductors (41, 42) which extend to the light entry end.

2. An optical waveguide as set forth in claim 1 characterized in that the tube (6) is freely rotatable.

3. An optical waveguide as set forth in claim 1 characterized in that the optical waveguide is a liquid optical waveguide and the wires or stranded conductors (41, 42) extend in the interior of the optical waveguide (2) but outside the liquid of the waveguide to the light entry end.

4. An optical waveguide as set forth in claim 1 characterized in that the tube (6) has a mechanical limiting means (31) which is fixed thereon and which limits displaceability of the magnet (26) in the axial direction of the tube (6).

5. An optical waveguide as set forth in claim 1 characterized in that the mechanical limiting means is a stopper ring (31) which limits the displaceability of the magnet (26) in a direction towards the magnetically activatable switch (27).

6. An optical waveguide as set forth in claim 5 characterized in that the displaceable magnet (26) is arranged in the interior of a sleeve (10) which surrounds the tube (6) and which is displaceable axially thereon.

7. An optical waveguide as set forth in claim 1 characterized by an element for producing a return force for the magnet (26).

8. An optical waveguide as set forth in claims 1 characterized in that
the hand switch is a magnetic flip switch in which the displaceable magnet (26) has a stable initial position and a stable switched position,
wherein the flip switch is formed by the co-operation
of the displaceable magnet (26)
with at least one second annular magnet (29) which is arranged in the interior of the tube (6) coaxially with respect to the magnet (26) and fixedly on the liquid optical waveguide (2) so that the magnet (26) which bears displaceably against the tube (6) fitted over the optical waveguide (2) can be pushed over the fixed magnet (29) and in that position forms the initial position which is stable by virtue of a metastable force equilibrium,
wherein the magnets (26) and (29) are so polarized that repulsion occurs between the fixed magnet (29) and the magnet (26) which is displaced in the direction of the magnetically activatable switch (27) and the displaceable magnet (26) assumes a stable switched position.

9. An optical waveguide as set forth in claim 8 characterized in that provided in coaxial relationship with the annular magnets (26, 29; 26a, 26b, 29; 26, 29a, 29b) and fixedly on the optical waveguide (2) is a further annular magnet (8) which serves for mechanically securing an applicator portion (7b) and which is positioned at the light exit end of the optical waveguide (2), wherein the magnets (29; 29a, 29b) and (8) are axially polarized and like magnetic poles of those magnets ((29; 29a, 29b) and (8) are disposed in directly opposite relationship and wherein the magnets (26, 29; 26a, 26b, 29; 26, 29a, 29b) and (8) are permanent magnets.

10. An optical waveguide as set forth in claim 9 characterized in that the magnets (8, 26, 29) used are optionally ring structures which are made up of a plurality of discrete circularly arranged sectors of magnetic material, wherein the magnetic material is a permanent magnet or a magnetizable material, or ring structures which are made up of magnetic foils curved in a ring shape.

11. An optical waveguide as set forth in claim 8 characterized in that the stable switched position of the displaceable magnet (26) is formed by a stopper ring (31).

12. An optical waveguide as set forth in claim 7 characterized in order to affect the return force arranged in the interior of the sleeve (10) are a spiral spring (24) and a cutting edge-shaped stopper ring (25) which is fixed on the tube (6), wherein the spiral spring (24) is disposed on one side of the stopper ring (25) and the magnet (26) is disposed on the other side.

13. An optical waveguide as set forth in claim 7 characterized in that to produce the return force arranged fixedly on the optical waveguide (2) in coaxial relationship with the magnet (26) is at least one fixed second annular magnet (29) so polarized that attraction occurs between it and the magnet (26) which is displaced in the direction of the magnetically activatable switch (27).

14. An optical waveguide as set forth in claim 13 characterized in that at least one of the magnets (26, 29) is a permanent magnet and the other magnet is optionally made from a magnetizable material.

15. An optical waveguide as set forth in claim 13 characterized in that the displaceable and the fixed magnets (26, 29) are axially polarized permanent magnets whose polarization axes face in the same direction.

16. An optical waveguide as set forth in claim 13 characterized in that either the fixed magnet (29) or the displaceable magnet (26) is a radially polarized permanent magnet.

17. An optical waveguide as set forth in claim 13 characterized in that both magnets (26, 29) are radially polarized permanent magnets.

18. An optical waveguide as set forth in claim 13 characterized in that the displaceable magnet (26) is a radially polarized permanent magnet and the fixed magnet (29) is an axially polarized permanent magnet.

19. An optical waveguide as set forth in claim 1 characterized by an arrangement of three mutually coaxial annular magnets which form a magnetic flip switch with a stable initial position and a stable switched position, wherein
(a) the arrangement includes two interconnected terminal magnets (26a, 26b; 29a, 29b) and a centrally disposed magnet (29; 26),
(b) the centrally disposed magnet (29; 26) and the terminal magnets (26a, 26b; 29a, 29b) are displaceable over each other in such a way that the centrally disposed magnet (29; 26) is arranged between the terminal magnets (26a, 26b; 29a, 29b) and in that position the magnet arrangement forms the initial position which is stable by virtue of a metastable force equilibrium, and
(c) to produce the stable switched position of the switch the magnets are so movable that either
(c1) the centrally disposed magnet (29) is stationary and the terminal magnets (26a, 26b) are displaceable relative thereto and to such an extent that they are stably positioned between the magnetically activatable switch (27) and the centrally disposed magnet (29), or
(c2) the terminal magnets (29a, 29b) are stationary and the centrally disposed magnet (26) is displaceable relative thereto and to such an extent that it is positioned stably between the magnetically activatable switch (27) and one of the terminal magnets (29b), wherein either
(c3) the terminal magnets (26a, 26b) are axially displaceable on the tube (6) but the centrally disposed magnet (29) is arranged fixedly on the optical waveguide (2), or
(c4) the centrally disposed magnet (26) is axially displaceable on the tube (6) but the terminal magnets (29a, 29b) are arranged fixedly on the optical waveguide (2),
wherein the displaceable magnet or magnets (26; 26a, 26b) are arranged optionally in the displaceable sleeve (10).

20. An optical waveguide as set forth in claim 19 characterized in that the stable switched position of the displaceable magnet or magnets (26; 26a, 26b) is formed by the stopper ring (31).

21. An optical waveguide as set forth in claim 1 characterized by at least two series-connected magnetically activated switches 27).

22. An optical waveguide as set forth in claim 1 characterized in that the magnetically activatable switch or switches (27) are reed switches or Hall switches.

23. An optical waveguide as set forth in claim 1 characterized in that the optical waveguide (2) is a liquid optical waveguide.

24. An optical waveguide as set forth in claim 6 characterized in that the sleeve (10) has at the light exit end a rotationally symmetrical finger grip recess (28) and optionally extending on its surface therearound a knurling (28a).

* * * * *